(12) United States Patent
Yu

(10) Patent No.: US 7,762,944 B2
(45) Date of Patent: Jul. 27, 2010

(54) DETACHABLE POROUS VAGINAL MOLD

(75) Inventor: Ken-Jen Yu, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 1273 days.

(21) Appl. No.: 10/829,594

(22) Filed: Apr. 22, 2004

(65) Prior Publication Data

US 2005/0240208 A1    Oct. 27, 2005

(51) Int. Cl.
*A61F 2/00* (2006.01)
(52) U.S. Cl. .......................................... 600/37
(58) Field of Classification Search .................. 600/37, 600/38, 33, 29, 208; 128/885, 897; 604/279, 604/275, 515; 606/191
See application file for complete search history.

(56) References Cited

U.S. PATENT DOCUMENTS

| | | | | |
|---|---|---|---|---|
| 5,013,297 A | * | 5/1991 | Cattanach | 604/515 |
| 5,256,123 A | * | 10/1993 | Reinbolt | 482/113 |
| 7,276,056 B2 | * | 10/2007 | Abbott et al. | 604/515 |
| 2002/0055723 A1 | * | 5/2002 | Liu et al. | 604/279 |
| 2003/0144639 A1 | * | 7/2003 | Gehling | 604/360 |

OTHER PUBLICATIONS

Dan Alessandrescu, et al., Neocolpopoiesis with split-thickness skin graft as a surgical treatment of vaginal agenesis: Retrospective review of 201 cases, American Journal of Obstretrics and Gynecology, pp. 131-138, Mosby-Year Book Inc., Jul. 1996.
Ken-Jun Yu, et al., A detachable porous vaginal mold facilitates reconstruction of a modified McIndoe neovagina, Fertility and Sterility, vol. 81, No. 2, pp. 435-439, American Society of Reproductive Medicine, Feb. 2004.

* cited by examiner

*Primary Examiner*—Charles A Marmor, II
*Assistant Examiner*—Christine D Hopkins
(74) *Attorney, Agent, or Firm*—The Webb Law Firm

(57) ABSTRACT

A detachable vaginal mold is provided. The detachable vaginal mold includes a main body, a minor part, and a jointing design formed between the main body and the minor part for connecting the main body to the minor part. The jointing design is one selected from a group consisting of a dentation design, a mortise design, a screw design, a mitre design, a fastener design, and a combination thereof.

8 Claims, 12 Drawing Sheets

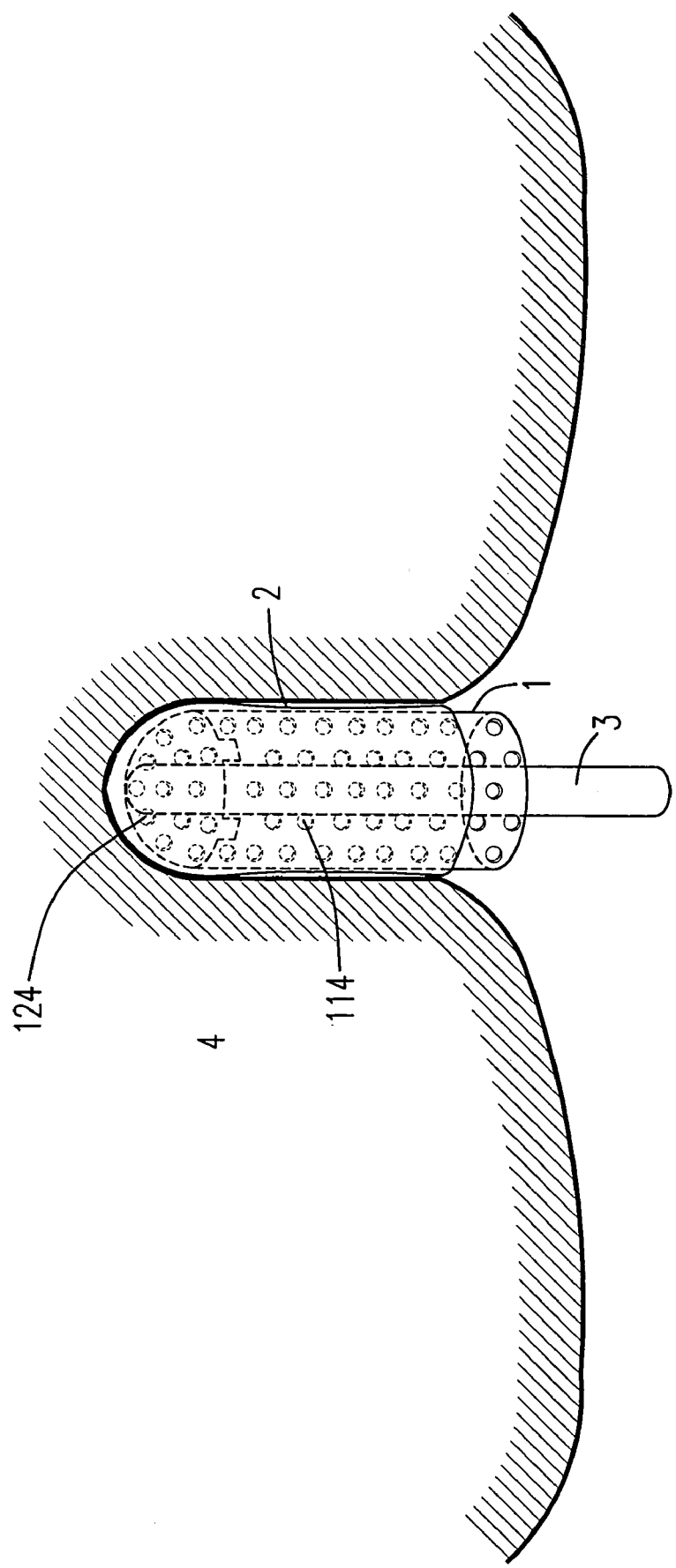

DETACHABLE POROUS VAGINAL MOLD

FIELD OF THE INVENTION

This invention relates to a vaginal mold, and particularly to a detachable vaginal mold used for vaginal reconstruction, vaginal creation and vaginal anaplasty.

BACKGROUND OF THE INVENTION

In general, reconstructing the vagina is necessary for patients of congenital vaginal abnormality, patients of congenital vaginal agenesis, and the transsexuals. In addition, since some people get vaginal injuries by accidents or diseases, to perform the vaginal reconstruction surgery to them is also necessary. However, at present, the skin graft vaginal reconstruction is the most common vaginal reconstruction. The skin graft vaginal reconstruction is a surgery that transplants some skin grafts into a creative vaginal cavity through a vaginal mold. After the skin grafts are attached onto the wall of the creative vaginal cavity, it's usually 10 to 14 days, the vaginal mold is removed from the patients. However, since the skin grafts are tightly covered onto the vaginal mold surface, the new healed vulnerable skin graft might be displaced, peeled off, inversed or even pulled off from the vaginal cavity wall along with the vaginal mold during the removal of the vaginal mold from the patients.

Sine the conventional vaginal mold is a solid column or a hollow column and has no drainage holes, it is difficult to observe the recovery of the graft and hard to change the medical dressings and take care of the vaginal wound. In addition, since the tissue fluid of the wound cannot be drained away successfully, it is possible to lead to the local complications including the graft maceration, sloughing, inflammation, infection, the perineum and other discomforts for the patients.

In order to solve the problem of the tissue fluid drainage, Alessanndrescu et al., had disclosed a vaginal mold with the porous sidewalls in the article "*Neocolpopoiesis with split-thickness skin graft as a surgical treatment of vaginal agenesis: Retrospective review of* 201 *cases*", Journal of Obstetrics and Gyneocology, Vol. 175 (1), pp. 131-138, 1996, as shown in FIG. 1. Since the disclosed porous vaginal mold has the openings for draining the tissue fluid, the complications to the tissue fluid are effectively avoided. However, how to prevent the skin grafts from being displaced, peeled off, inversed, or pulled off during the removal of the vaginal mold from the patients is still unsolved.

In the view of the foresaid discussion, a new vaginal mold with suitable draining ability, easier removal ability, better wound care capability, and so on is the expectancy.

SUMMARY OF THE INVENTION

It is an object of the present invention to provide a detachable vaginal mold. The detachable vaginal mold includes a main body, a minor part, and a jointing design formed between the main body and the minor part for connecting the main body to the minor part.

Preferably, the main body is a hollow columnar structure.

Preferably, the minor part covers one end of said main body.

Preferably, the main body is a porous structure.

Preferably, the minor part has an arc surface.

Preferably, the minor part is porous.

Preferably, the jointing design is one selected from a group consisting of a dentation design, a mortise design, a screw design, a mitre design, a fastener design, and a combination thereof.

Preferably, the minor part serves as a front end of said vaginal mold.

In accordance with another aspect of the present invention, a detachable columnar-hollow vaginal mold composed of plural petal structures is provided.

Preferably, the plural petal structures are porous.

Preferably, the plural petal structures are connected mutually by a design selected from a group consisting of a dentation design, a mortise design, a mitre design, a fastener design, and a combination thereof.

Preferably, the detachable columnar-hollow vaginal mold is an one-end opened hollow structure.

In accordance with another aspect of the present invention, a detachable columnar-hallow vaginal mold comprised of plural structures is provided. In which, the plural structures are connected mutually by a design selected from a group consisting of a dentation design, a mortise design, a mitre design, a fastener design, and a combination thereof.

Preferably, the plural petal structures are porous.

Preferably, the plural structures are identical structures.

Preferably, the plural structures are different structures.

Preferably, some of the plural structures are different structures and others are identical The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
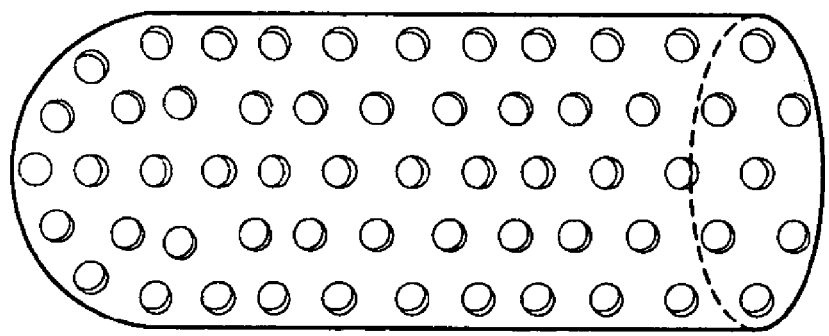
FIG. 1 is a vaginal mold according to the prior art.
Figure 2A:
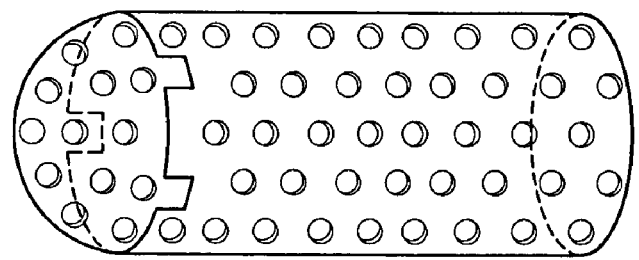
FIGS. 2 (A)-(B) show the detachable porous vaginal mold. according to the first preferred embodiment of the present invention.
Figure 2B:
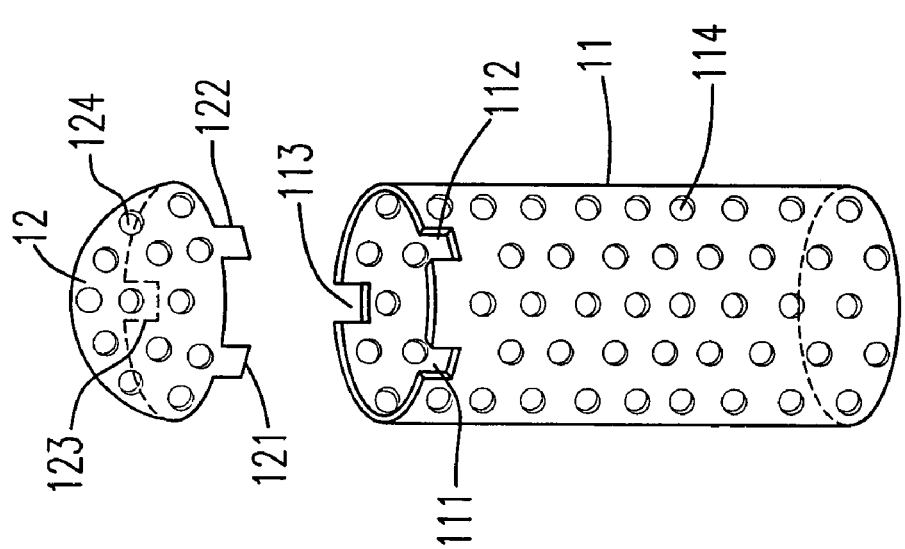
Figure 3A:
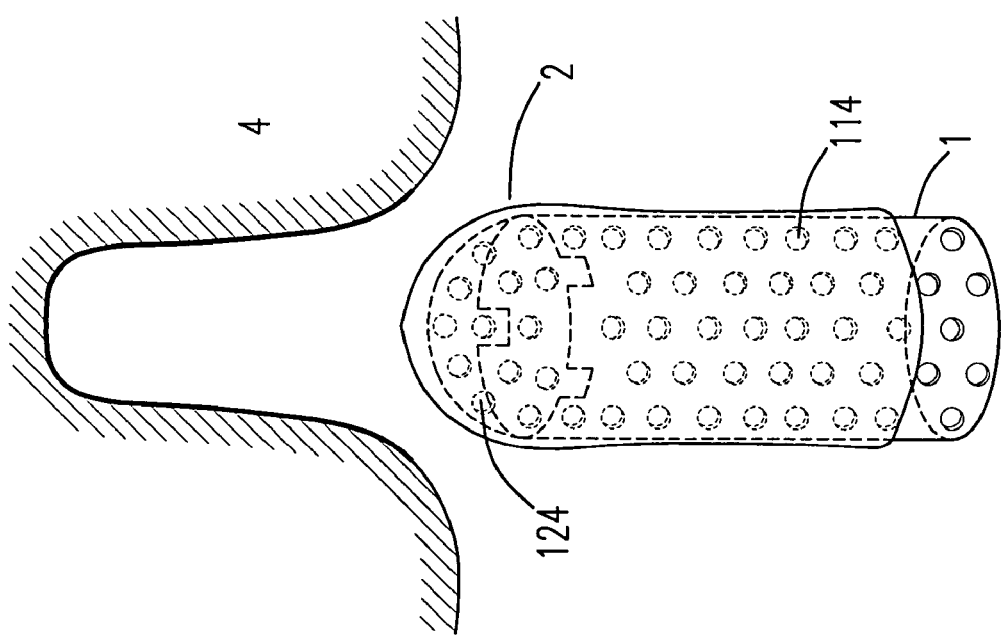
FIGS. 3 (A)-(E) are the schematic diagrams showing the implement of the artificial skin graft performed with the detachable porous vaginal mold according to the first preferred embodiment of the present invention.
Figure 3B:
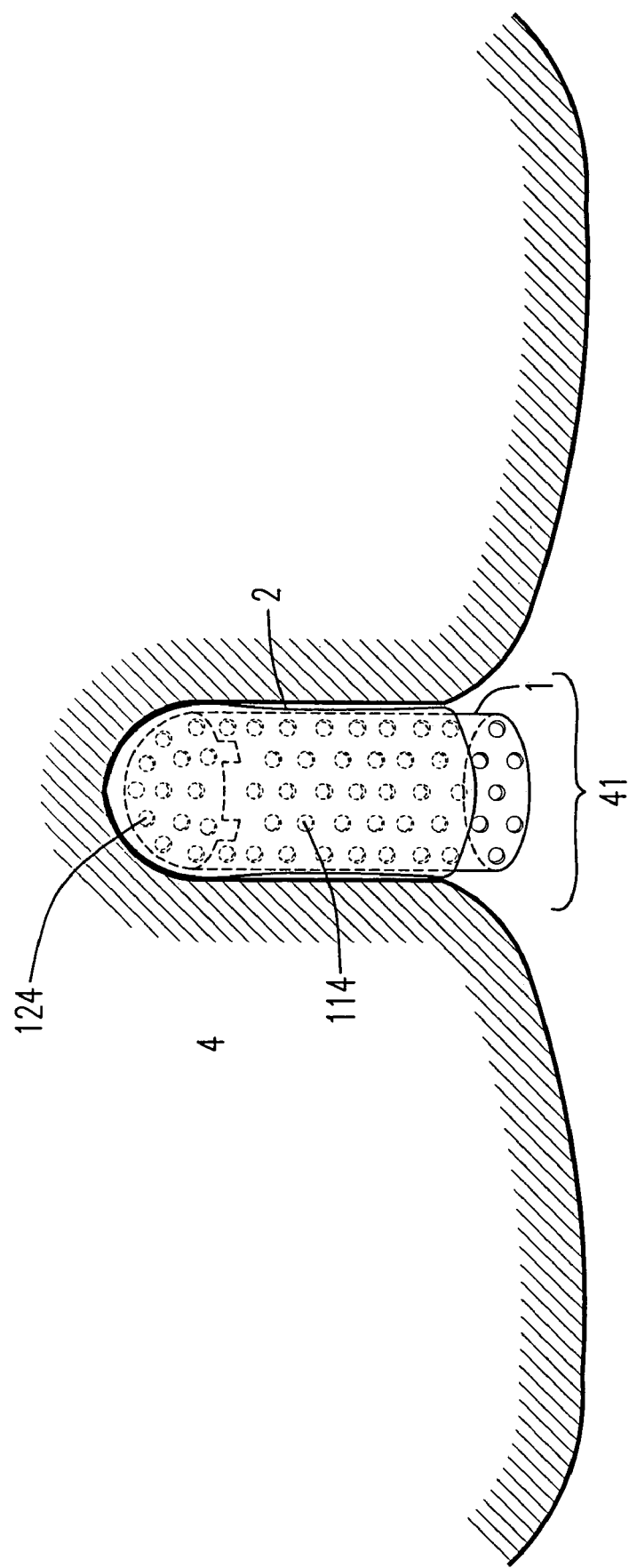
Figure 3D:
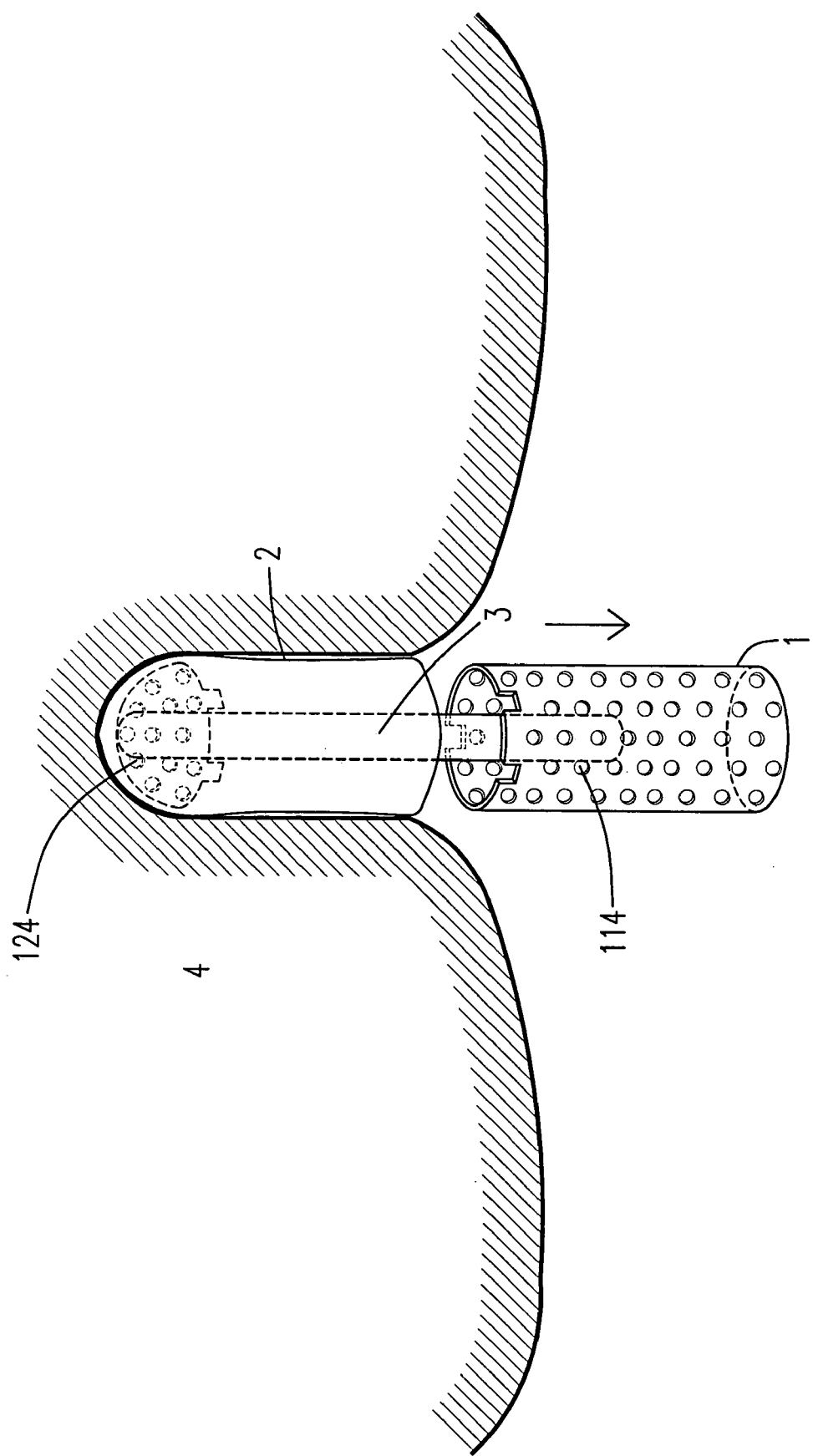
Figure 3E:
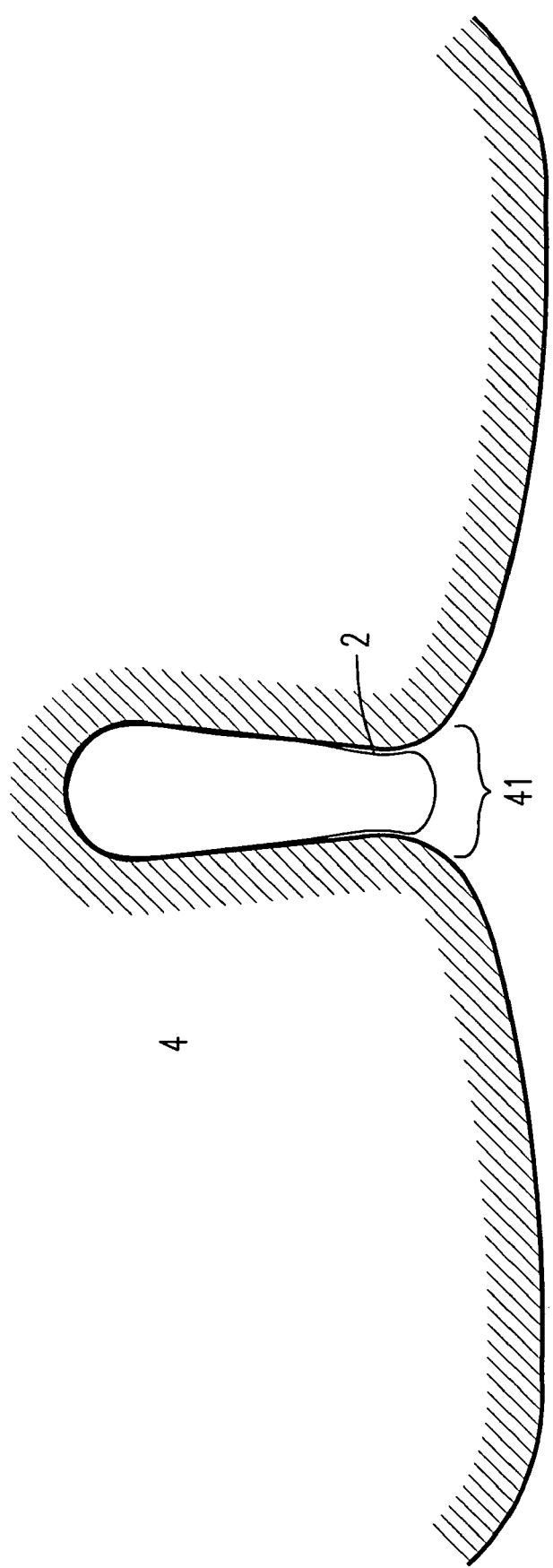

Please refer to FIGS. 2 (A)-(B), which are the vaginal molds according to the first preferred embodiment of the present invention. As shown in FIGS. 2 (A)-(B), the vaginal mold 1 is a hollow column-including the main body 11 and the top minor part 12. Three concave jointing structures 111, 112, 113 are located on the main body 11, and three protrudent jointing structures 121, 122, and 123 are located on the top minor part 12. In which, the concave jointing structures 111, 112, 113 are respectively dovetailed to the protrudent jointing structures 121, 122, and 123 for preventing the relative movements from happening between the main body 11 and the top minor part 12. In addition, the main body 11 includes a plurality of draining openings 114 and the top minor part 12 includes a plurality of draining openings 124 as well. The draining openings 114 and 124 are suitable for taking care of the wounds.

In this embodiment, a 50-ml conical plastic centrifuge tube with the thickness of 3 mm, the length of 12 cm and the diameter of 3 cm is used to manufacture the vaginal mold 1. In which, the draining openings 114 and 124 with the diameters of 2 mm are constructed by the general dentistry technology. Furthermore, the length of the main body 11 is 10.5 cm, and the length of the top minor part 12 is 1.5 cm. In view of the aforesaid description, since the embodiment according to the present application is able to be achieved by a general centrifuge tube, so that the relevant cost is obviously reduced. In addition, since there exist individual differences among different patients, the lengths, the sizes, the thicknesses, the diameters, and the shapes of the vaginal mold, the sizes of the openings for draining, and the materials of the vaginal mold are able to be adjusted by the patients' personal specific needs. Therefore, the applications of the vaginal molds according to the present invention are really wide, and the relevant forms of the vaginal molds should not be limited to the embodiments according to present invention. In addition, it should be noted that since the vaginal mold might be cut short and the sections might be very sharp, the vaginal mold might be further combined with a protecting device, such as a rubber ring, for preventing the patient from being cut by the sections.

Please refer to FIGS. 3 (A)-(B), which are the schematic diagrams showing the implement of the artificial skin graft performed with the vaginal mold according to the first preferred embodiment of the present invention. As shown in FIG. 3 (A), the full-thickness skin graft (FTSG) 2 taken from the inguinal regions is sewn over the vaginal mold 1. Then, the vaginal mold 1 with the FTSG 2 is inserted into the patient 4, as shown in FIG. 3 (B). Since there exist the draining openings 114 and 124 on the walls of the vaginal mold 1, the tissue fluid secreted from the wound is able to flow into the vaginal mold 1. Therefore, the local complications including the graft maceration, sloughing, inflammation, infection, and the perineum are able to be avoided. In addition, it is also possible to apply the medications to the wounds, so as to clean the wounds or to reduce inflammations of the wounds via the draining openings 114 and 124, if necessary. Furthermore, since the vaginal mold 1 is a hollow column, it is possible to place a piece of sterile gauze or something like that into the vaginal mold 1 for absorbing the tissue fluid and further to determine the recoveries of the wounds according to the colors and the smell of the absorbed tissue fluid. In addition, it is also possible to proceed some tissue cultures and some medical tests to the absorbed tissue fluid in order to obtain some information for remedying.

When the healings of the wounds are good enough (about 10 to 14 days), the support 3 is used to hold the top minor part 12 via the inner of the main body 11, as shown in FIG. 3 (C). Afterward, the main body 12 is removed from the patient 4, as shown in FIG. 3(D). After that, the vagina opening 41 is opened by a speculum (not shown) and the top minor part 12 is removed with a pair of forceps without difficulty, as shown in FIG. 3 (E). During the process of removing the main body 11, since the FTSG 2 is hold by the support 3 via the top minor part 12, the FTSG 2 would not be displaced, peeled off, inversed, or pulled off during the process of removing the vaginal mold 1 from the patient 4. To sum up, the success of the vaginal reconstruction is significantly improved by the vaginal mold according to the present invention.

Figure 4B:
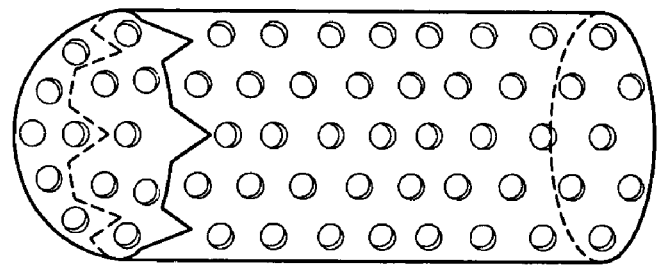
FIGS. 4 (A)-(B) show the detachable porous vaginal mold according to the second preferred embodiment of the present invention.
Figure 4A:
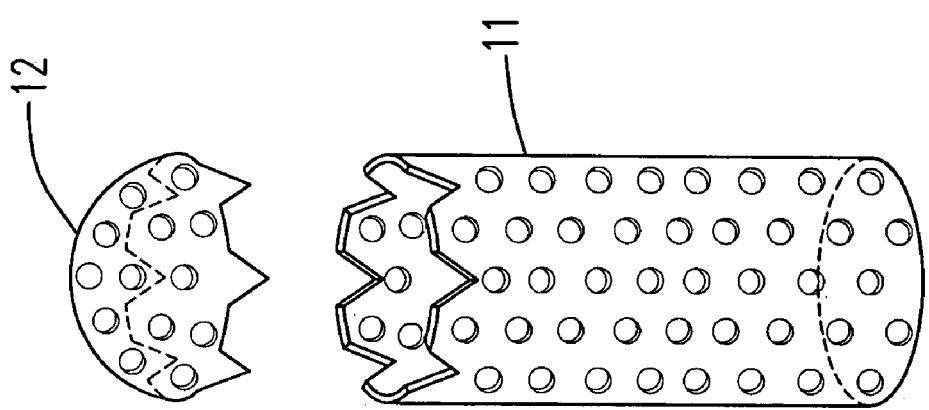

Please refer to FIGS. 4 (A)-(B), which are the schematic diagrams showing the vaginal mold according to the second preferred embodiment of the present invention. As shown in FIGS. 4 (A)-(B), the vaginal mold 1 is formed by connecting the main body 11 to the top minor part 12 via a dentation design.

Figure 5B:
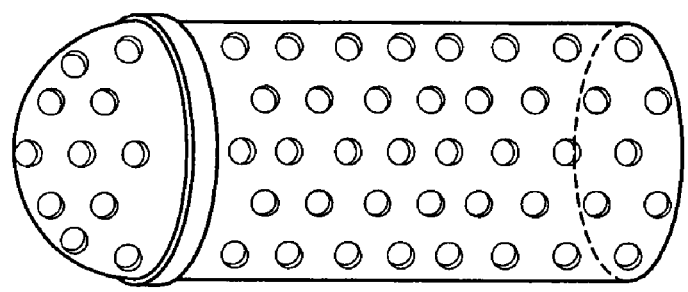
FIGS. 5 (A)-(B) show the detachable porous vaginal mold according to the third preferred embodiment of the present invention FIGS. 6 (A)-(B) show the detachable porous vaginal mold according to the forth preferred embodiment of the present invention.
Figure 5A:
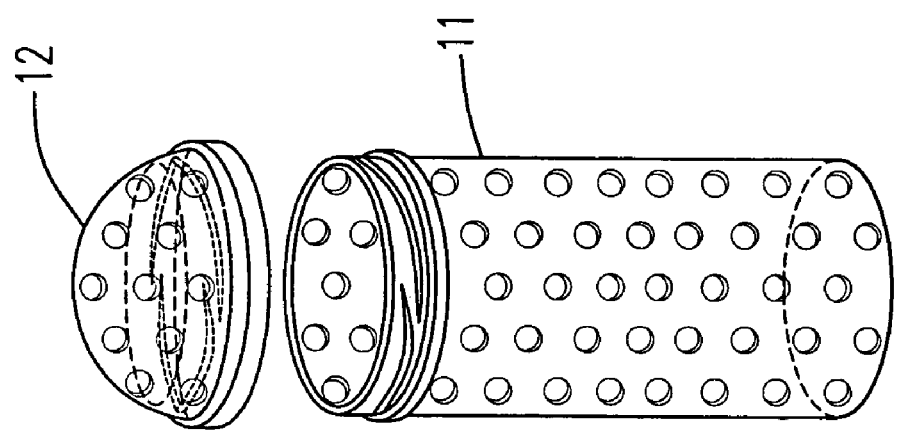

Please refer to FIGS. 5 (A)-(B), which are the schematic diagrams showing the vaginal mold according to the third preferred embodiment of the present invention. As shown in FIGS. 5 (A)-(B), the vaginal mold 1 is formed by connecting the main body 11 to the top minor part 12 via a screw design.

Figure 6B:
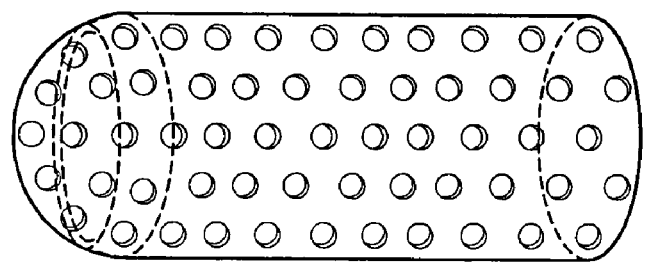
Figure 6A:
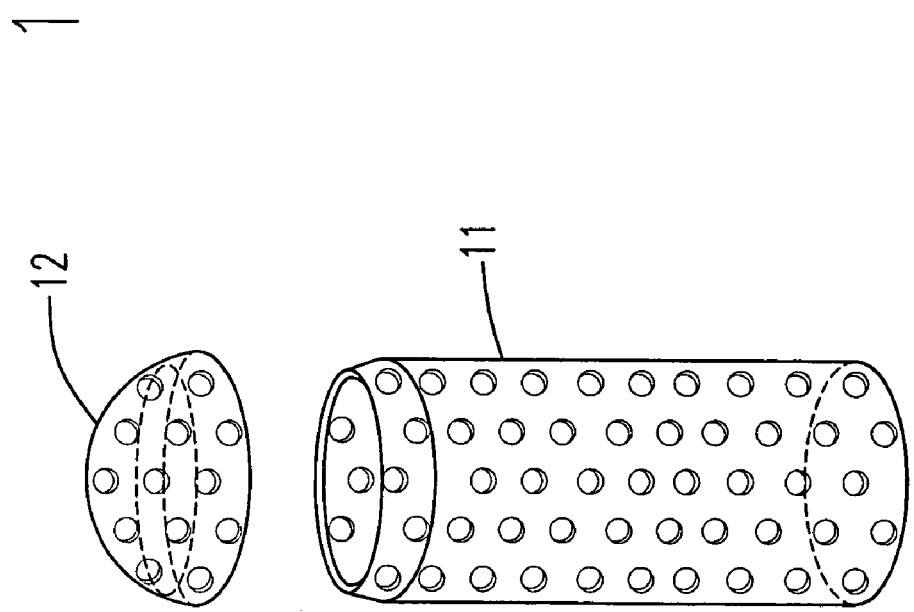

Please refer to FIGS. 6 (A)-(B), which are the schematic diagrams showing the vaginal mold according to the fourth preferred embodiment of the present invention. As shown in FIGS. 6 (A)-(B), the vaginal mold 1 is formed by connecting the main body 11 to the top minor part 12 via a mitre design.

Figure 7C:
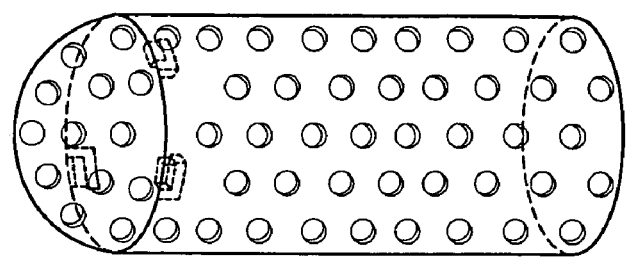
FIGS. 7 (A)-(C) show the detachable porous vaginal mold according to the fifth preferred embodiment of the present invention.
Figure 7B:
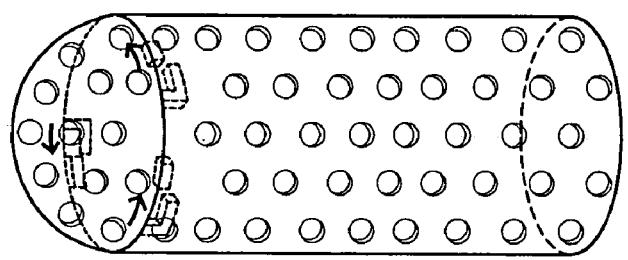
Figure 7A:
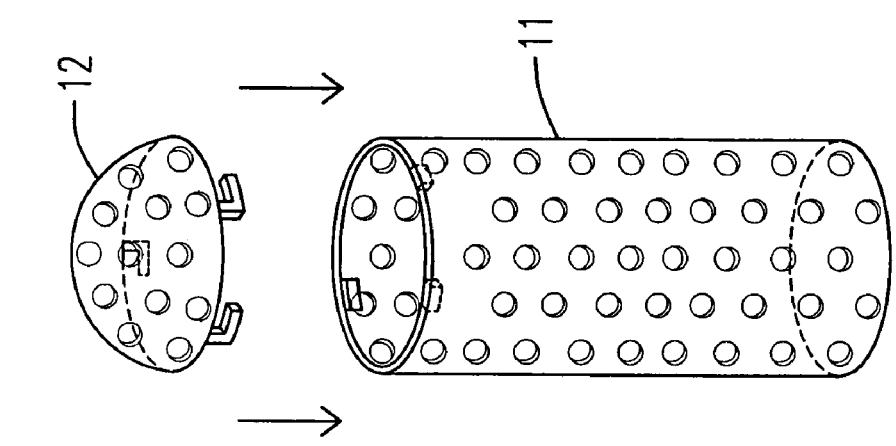

Please refer to FIGS. 7 (A)-(C), which are the schematic diagrams showing the vaginal mold according to the fifth preferred embodiment of the present invention. As shown in FIGS. 7 (A)-(C), the vaginal mold 1 is formed by connecting the main body 1 i to the top minor part 12 via a fastener design.

Figure 8B:
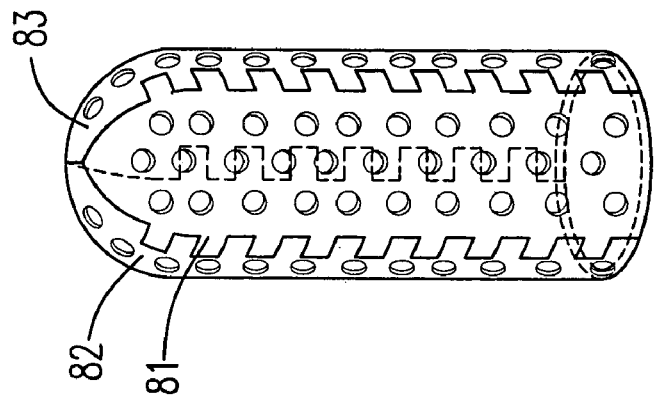
FIGS. 8 (A)-(B) show the detachable porous vaginal mold according to the sixth preferred embodiment of the present invention.
Figure 8A:
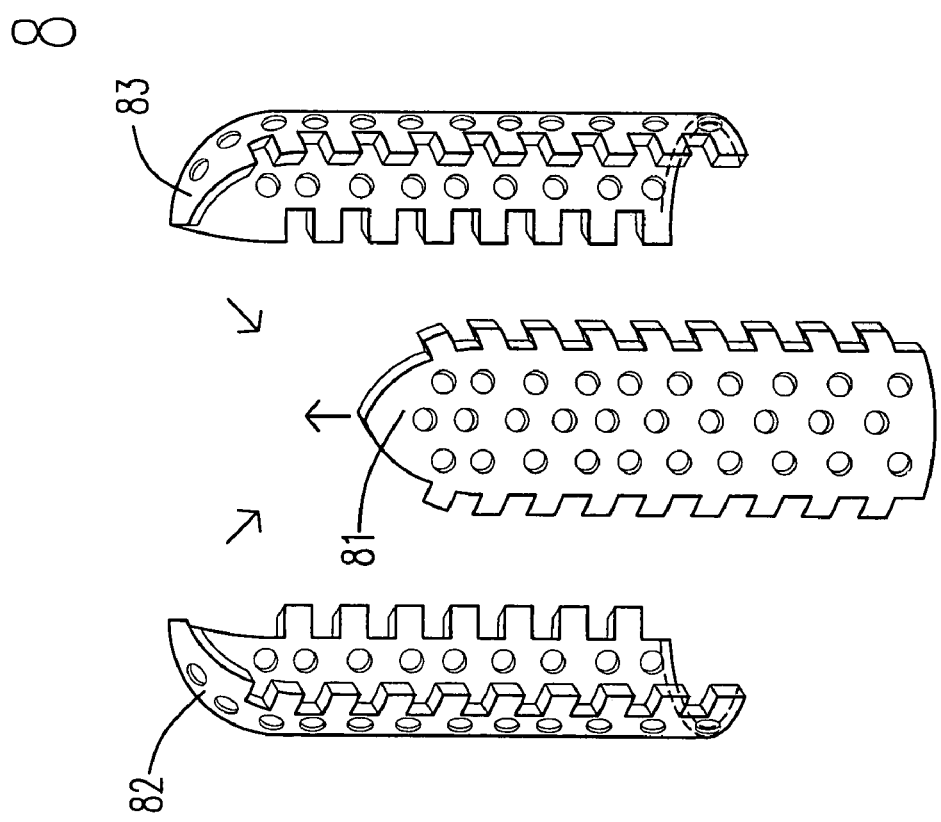

Please refer to FIGS. 8 (A)-(B), which are the schematic diagrams showing the vaginal mold according to the sixth preferred embodiment of the present invention. As shown in FIGS. 8 (A)-(B), the vaginal mold 8 is formed by connecting the petal structures 81, 82 and 83 together via the mortise design. During the operation, once the recoveries of the wounds are good enough (about 10 to 14 days), one petal structure, such as petal structure 81, is first taken apart inwardly and removed from the other two petal structures, such as the petal structures 82 and 83, and then the remained petal structures are taken apart, too. However, since the possibilities of skin graft being displaced, peeled off, inversed, or pulled off are corresponding to the areas of the removal components of the vaginal mold, to reduce the area of each petal structure (or to increase the amount of the petal structures) is preferable for reducing the possibilities that the skin graft is displaced, peeled off, inversed, or pulled off. In addition, it should be noted that the vaginal mold 1 shown in FIGS. 8 (A)-(B) is capable to be formed from several similar petal structures or dissimilar petal structures.

To sum up the above discussions, the advantages and features of the vaginal mold according to the present invention could be summarized as follows:

1. Since there exist some openings on the walls of the vaginal mold, the tissue fluid is able to be removed and the complications including the graft maceration, sloughing, inflammation, infection, and the perineum and the genital inflammations are able to be avoided.

2. Since the tissue fluid could be removed by being absorbed by a piece of sterile gauze or something like, and the recoveries of the wounds could be determined according to the colors and the smell of the absorbed tissue fluid, the wound cares are much better than before.

3. Since the vaginal mold of the present invention is a detachable design, which is suitable for being removed from the vaginal cavity step by step, the probabilities of the skin graft being displaced, peeled off, inversed, or even pulled off from the vaginal cavity walls are significantly reduced.

In view of the foresaid discussions, it is known to one skilled in the art that the vaginal mold of the present invention does have the novelty, the progressiveness, and the utility.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

Some relevant contents of the present invention have been published in *Fertility and Sterility* (Yu K J, Lin Y S, Chao K C, Chang S P, Lin L Y, Bell W. A detachable porous vaginal mold facilitates reconstruction of a modified McIndoe neovagina. *Fertility and Sterility*. Vol. 81(2): 435-439. 2004.

What is claimed is:

1. A vaginal mold detachable in a reconstructed vagina, comprising:
    a porous main body having a hollow columnar structure and a first jointing structure, wherein the porous main body is capable of supporting said reconstructed vagina;
    a porous minor part being a front end of said vaginal mold and having a second jointing structure connected to said first jointing structure, wherein the porous minor part is capable of supporting said reconstructed vagina, and is detachable from said porous main body inside of said reconstructed vagina, and both of the porous main body and the porous minor part are independently removable from said reconstructed vagina; and
    a support capable of holding said porous minor part when said porous main body is detached from said porous minor part and removed from said reconstructed vagina.

2. The vaginal mold as claimed in claim 1, wherein said porous minor part covers one end of said porous main body.

3. The vaginal mold as claimed in claim 1, wherein said porous minor part has an arc surface.

4. The vaginal mold as claimed in claim 1, wherein each of said first and second jointing structures is one selected from a group consisting of a dentation structure, a mortise structure, a screw structure, a mitre structure, a fastener structure and a combination thereof.

5. The vaginal mold as claimed in claim 1, wherein said porous main body and said porous minor part have plural openings configured thereon.

6. The vaginal mold as claimed in claim 5, wherein said plural openings are plural draining openings and pass therethrough a tissue fluid.

7. The vaginal mold as claimed in claim 1, wherein said porous main body and said porous minor part are covered by a full-thickness skin graft (FTSG).

8. The vaginal mold as claimed in claim 1, being used for a vaginal reconstruction.

\* \* \* \* \*